(12) United States Patent
Durand et al.

(10) Patent No.: US 7,680,538 B2
(45) Date of Patent: Mar. 16, 2010

(54) METHOD OF TREATING OBSTRUCTIVE SLEEP APNEA USING ELECTRICAL NERVE STIMULATION

(75) Inventors: Dominique M. Durand, Solon, OH (US); Paul Byongsuk Yoo, Greensboro, NC (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 11/109,338

(22) Filed: Apr. 19, 2005

(65) Prior Publication Data

US 2006/0224211 A1  Oct. 5, 2006

Related U.S. Application Data

(60) Provisional application No. 60/667,136, filed on Mar. 31, 2005.

(51) Int. Cl.
*A61N 1/18* (2006.01)
(52) U.S. Cl. .......................... 607/42; 607/48
(58) Field of Classification Search ................ 607/42, 607/2, 48, 26; 600/26
See application file for complete search history.

(56) References Cited

U.S. PATENT DOCUMENTS

| 4,830,008 | A |  | 5/1989 | Meer |
| 5,065,756 | A |  | 11/1991 | Rapoport |
| 5,245,995 | A |  | 9/1993 | Sullivan |
| 5,324,322 | A |  | 6/1994 | Grill |
| 5,344,438 | A |  | 9/1994 | Testerman |
| 5,483,969 | A |  | 1/1996 | Testerman |
| 5,540,733 | A |  | 7/1996 | Testerman |
| 5,549,655 | A |  | 8/1996 | Erickson |
| 5,591,216 | A | * | 1/1997 | Testerman et al. ............ 607/42 |
| 5,824,027 | A |  | 10/1998 | Andres |
| 5,919,220 | A |  | 7/1999 | Stieglitz |
| 6,212,435 | B1 | * | 4/2001 | Lattner et al. ............... 607/134 |
| 6,292,703 | B1 |  | 9/2001 | Meier |
| 6,366,815 | B1 |  | 4/2002 | Haugland |
| 6,456,866 | B1 |  | 9/2002 | Tyler |
| 6,587,725 | B1 |  | 7/2003 | Durand |
| 6,600,956 | B2 |  | 7/2003 | Maschino |
| 6,636,767 | B1 |  | 10/2003 | Knudson |
| 6,641,542 | B2 |  | 11/2003 | Cho |
| 2001/0010010 | A1 |  | 7/2001 | Richmond |
| 2002/0049479 | A1 | * | 4/2002 | Pitts ............................ 607/42 |
| 2003/0153953 | A1 | * | 8/2003 | Park et al. ..................... 607/17 |
| 2004/0073272 | A1 |  | 4/2004 | Knudson |
| 2005/0085874 | A1 | * | 4/2005 | Davis et al. ................... 607/66 |

* cited by examiner

*Primary Examiner*—Mark W Bockelman

(57) ABSTRACT

A method for treating a medical condition, such as obstructive sleep apnea, includes the step of stimulating a nerve, particularly the hypoglossal nerve, using at least one of the following techniques: (a) continuous low-level electrical stimulation; (b) electrical stimulation synchronized with a physical process, such as inspiration, without feedback from the nerve being stimulated; and (c) intermittent electrical stimulation at controlled intervals based on the patient's metabolism.

1 Claim, 1 Drawing Sheet

METHOD OF TREATING OBSTRUCTIVE SLEEP APNEA USING ELECTRICAL NERVE STIMULATION

This application is a continuation of U.S. Patent Application No. 60/667,136 filed Mar. 31, 2005, which is hereby incorporated herein by reference in its entirety.

FIELD OF THE INVENTION

The present invention relates to a method for treating a medical condition using electrical nerve stimulation, and more particularly to a method for treating obstructive sleep apnea by electrically stimulating the hypoglossal nerve.

BACKGROUND

Sleep apnea is characterized by temporary cessation of breathing during sleep, which can lead to or aggravate many health problems. Obstructive sleep apnea (often abbreviated OSA) is primarily caused by the collapse of the upper airway. The base of the tongue has been found to be a common site of obstruction in the upper airway, and the upper airway dilator muscles have been recognized as being important in maintaining an open airway.

Unfortunately, current treatment methods for obstructive sleep apnea have not been consistently effective for all patients. The standard method is Continuous Positive Airway Pressure (CPAP) treatment, which requires the patient to wear a mask through which air is blown into the nostrils to keep the airway open. Patient compliance is poor due to discomfort and side effects, such as sneezing, nasal discharge, and dryness. A more recent treatment option, the implantation of rigid inserts in the soft palate to provide structural support, is both more invasive and generally is only effective for mild to moderate cases of obstructive sleep apnea. Alternative treatments are even more invasive and drastic, including tracheostomy and tissue ablation (somnoplasty or uvulopalatopharyngoplasty (UPPP)). Electrical stimulation of muscles has become another recent treatment option. These treatments have included direct electrical stimulation of muscle fibers, as disclosed in U.S. patent application Publication No. 2001/0010010 A1, and electrical stimulation of the hypoglossal nerve in a closed-loop system based on feedback from signals naturally occurring in the hypoglossal nerve, as disclosed in U.S. Pat. No. 6,456,866, for example.

SUMMARY

The present invention provides a method for treating a medical condition, such as obstructive sleep apnea, by directly electrically stimulating a nerve to activate one or more muscles rather than electrically stimulating the muscle fibers directly. The method includes stimulating a nerve using at least one of the following techniques: (a) continuous electrical stimulation where a low level of stimulation is provided to maintain the stiffness of the airway throughout the respiratory cycle; (b) intermittent electrical stimulation initiated in response to sensing a physical process, such as inspiration, sensed by a remote sensor without feedback from the nerve being stimulated; or (c) intermittent electrical stimulation at controlled intervals, predetermined based on the patient's resting nighttime metabolism, determined by observing the nighttime respiratory rate, for example. Although other medical conditions might be successfully treated with this method, this method is well suited for the treatment of obstructive sleep apnea.

Specifically, a method in accordance with the invention includes controlling the patency of a patient's airway by electrically stimulating a nerve to activate an upper-airway controlling muscle, including intermittently stimulating the nerve at predetermined intervals based on a patient's metabolism.

Another method in accordance with the invention includes continuously electrically stimulating at least one fascicle of the hypoglossal nerve at a predetermined amplitude of about 10% less than the threshold amplitude necessary to activate a muscle of a patient up to approximately the patient's threshold activation amplitude.

Yet another method in accordance with the invention includes electrically stimulating a nerve and initiating the stimulation in response to a physical process other than a signal from the nerve being stimulated.

Electrically stimulating the nerve requires less power to activate the muscles than stimulating the muscle fibers directly. Stimulating the nerve also activates an entire muscle, rather than simply the muscle fibers being stimulated. Direct nerve stimulation also provides the opportunity for directing the stimulation to fascicles of the nerve to tune the stimulation for the desired outcome.

Hypoglossal nerve stimulation overcomes the side effects of the CPAP treatment mentioned above. The mask used for treatment with CPAP is not needed for hypoglossal nerve stimulation, which also prevents or minimizes problems with skin irritation, claustrophobia and panic attacks. All of these factors facilitate increased patient compliance, while being relatively less invasive than other currently-used surgical alternatives, and also being more cosmetically appealing. Thus, this invention addresses the need to provide a simple but effective method of stimulating a nerve to treat and/or prevent collapse of the upper airway during sleep.

The foregoing and other features of the invention are hereinafter fully described and particularly pointed out in the claims, the following description and annexed drawings setting forth in detail a certain illustrative embodiment of the invention, this embodiment being indicative, however, of but one of the various ways in which the principles of the invention might be employed.

DETAILED DESCRIPTION

Figure 1:
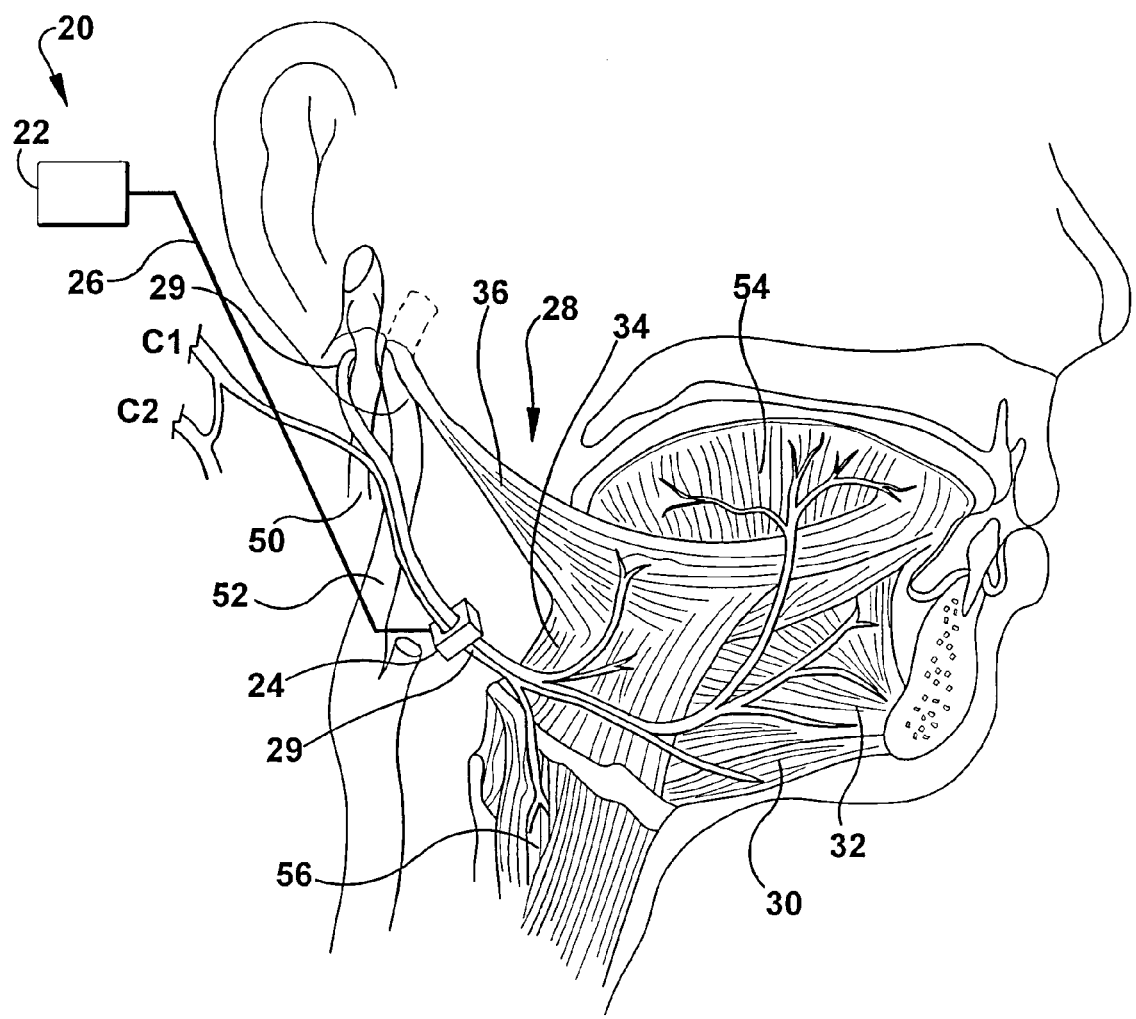
FIG. 1 is a schematic illustration of an apparatus and the nerves and muscles used in treating obstructive sleep apnea.

The present invention provides a method for treating a medical condition, such as obstructive sleep apnea, by electrically stimulating a nerve to control one or more muscles to achieve a desired effect for a patient. In the case of obstructive sleep apnea, electrical stimulation of the hypoglossal nerve, for example, can maintain the patency of the upper airway by activating the upper airway dilator muscles, thereby minimizing or eliminating airway collapse during sleep. Electrical stimulation of the lingual nerve also could relieve obstruction by activating the lingual-hypoglossal reflex loop.

More particularly, a method provided in accordance with the invention includes controlling the patency of a patient's airway by stimulating a nerve using at least one of the following techniques: (a) continuously electrically stimulating at least one fascicle of the hypoglossal nerve at a predetermined a low level amplitude throughout the respiratory cycle; (b) electrically stimulating a nerve and initiating the stimulation in response to a physical process, such as inspiration, using a remote sensor, without feedback from the nerve being stimulated; and (c) intermittently electrically stimulating a nerve at controlled intervals, predetermined based on the patient's resting nighttime metabolism, which can be determined from the patient's observed respiratory rate, for example.

An exemplary apparatus 20 for stimulating a nerve in accordance with the present invention is shown schematically in FIG. 1. The apparatus 20 includes a control system 22 (shown schematically) for generating the desired electrical stimulus, and an electrode 24 connected to the nerve to transmit the electrical stimulus to the nerve. The electrode 24 preferably is a cuff electrode that provides an intimate connection to the nerve. The cuff electrode 24 can have a variety of geometries or configurations, but preferably provides an intimate connection around the nerve. A lead wire 26 connects the electrode 24 to the control system 22 in the illustrated embodiment.

The control system 22 typically includes a battery, either primary or rechargeable, for powering the apparatus 20. The control system 22 also typically includes a processor for setting up stimulation parameters to achieve the desired outcome for the individual patient or otherwise controlling the stimulation. By way of example, these parameters can include stimulation amplitude, stimulation frequency and stimulation duration. In addition, the control system 22 typically includes a mechanism that allows the patient to turn the apparatus 20 on and off and possibly make adjustments within preprogrammed settings.

The control system 22 controls the application of the electrical stimulation based on programmed parameters and can take many forms. Portions of the control system 22, in addition to the electrode 24, can be implanted in the patient's body. Other portions of the control system 22 can be external to the body, and variations can exist between different control systems. For example, the control system 22 can include an implantable pulse generator (IPG) implanted in the body of the patient. As another example, in a different embodiment the IPG can be located within the electrode itself, with information and power supplied from the controller by light or other electromagnetic means.

The method provided by the invention is not limited by the design of the apparatus used to carry it out. For further information regarding an exemplary apparatus for practicing the method of the invention, refer to U.S. Pat. No. 6,587,725, which is hereby incorporated herein by reference in its entirety.

Although this method can be applied to other medical conditions where stimulation of a nerve would produce therapeutic or functional outcomes for a patient's airway, the method described in the following paragraphs focuses on the treatment of obstructive sleep apnea. In particular, the method addresses the problem of preventing or treating collapse of the upper airway 28 as a cause of obstructive sleep apnea. One solution presented is stimulation of the hypoglossal nerve (CN XII) to activate muscles that open the upper airway and/or maintain the stiffness of the airway to prevent collapse during sleep.

As shown in FIG. 1, the muscles that control the upper airway 28 and are innervated by the hypoglossal nerve 29 include the geniohyoid muscle 30, the genioglossus muscle 32, the hyoglossus muscle 34 and the styloglossus muscle 36. The genioglossus 32 is the main tongue protruder (the muscle that pushes the tongue out) and plays an important role in maintaining the patency of the upper airway. For reference, FIG. 1 also shows the vagus nerve 50, the internal carotid artery 52, the intrinsic muscles of the tongue 54 and the thyrohyoid muscle 56. Other structures in the area, such as the ear, nose and mouth also are schematically illustrated and should be apparent.

Selective activation of one or more of the muscles in the upper airway 28 can be effective in reducing the severity of sleep apnea and improving airway patency. Moreover, selectively stimulating various fascicles of the nerve can minimize the number of activated nerve branches while maximizing the therapeutic effectiveness of the stimulation. Fascicles of the hypoglossal nerve 29 can be individually stimulated to activate functionally similar muscles (for example, the genioglossus and geniohyoid muscles 32 and 42, which protrude the tongue and cause anterosuperior movement of the hyoid bone, respectively) to increase the patency of the upper airway. In some cases, activating functionally opposite muscles (for example, the genioglossus and the styloglossus muscles 32 and 36), also has been found to be effective in stiffening the airway to reduce the risk of collapse. This is probably related to the fact that the toungue protruder muscles generally are stronger than the tongue retractor muscles. Thus, co-activation of the tongue protruder and retractor muscles can have a synergistic effect that is advantageous during inspiration. While co-activation of the nerve branches innervating the tongue protruder and retractor muscles can be used during inspiration (as mentioned above) selective activation of the medial branch (innervating the genioglossus muscle 32) alone or as part of stimulating the entire nerve generally is effective for expiration.

The threshold amplitude for muscle activation will vary from one patient to the next. To ensure an adequate response, the stimulation parameters are adjusted to stimulate at an amplitude of about 10% below the patient's muscle activation threshold to about 20% over the patient's muscle activation threshold. The amplitude of the electrical stimulation typically is about 200 microamps ($\mu$A) to about 500 milliamps (mA). Other suitable combinations of stimulation amplitude and frequency can be provided on a patient-dependent basis. For example, the electrical stimulation can be provided by pulse trains of an intermittent duration or continuously, at a frequency of about 10 Hertz (Hz) to about 30 Hertz (Hz), with a pulse width of about 50 microseconds ($\mu$s).

In a first embodiment of the method, the electrical stimulation can be provided to the hypoglossal nerve continuously throughout the respiration cycle, during both inspiration (breathing in) and expiration (breathing out) phases, to maintain the desired muscle tone for patency of the upper airway. This is the simplest open-loop control system for maintaining the patency of the airway. Either the whole nerve is stimulated, or preferably one or more fascicles of the hypoglossal nerve are stimulated continuously to selectively activate the desired muscle or muscles. The stimulation has a relatively low amplitude, typically from about 10% below the patient's threshold amplitude up to the threshold amplitude. In this method, the added stimulation can be sufficient to activate the muscles on its own or can supplement and thereby amplify the electrical signals typically occurring in the hypoglossal nerve such that the combined amplitude is sufficient to activate the muscles and thereby reduce the risk of collapse of the patient's airway.

In a second embodiment of the method, the initiation of the electrical stimulation can be synchronized with a physical process, such as inspiration sensed by a remote sensor, without feedback from the nerve being stimulated. Thus the system can include one or more sensors for detecting a physical process, such as inspiratory efforts (i.e. the beginning of an attempt to breathe), for example, other than through the signals present in the hypoglossal nerve itself for activating the muscles. Various types of sensors are well known, including a pressure transducer for monitoring the pressure in the upper airway, and sensors that detect movement of the chest wall. While this system does use input from sensors to determine when to initiate a stimulation cycle, the input is from a separate sensor and not feedback from the nerve being stimulated, as is the case in a closed-loop system. In this system, no analysis has to be made of the signal from the nerve being stimulated.

According to a variation of this method, the stimulation can be applied to the lingual nerve in place of or in addition to stimulation applied to the hypoglossal nerve. The lingual nerve is primarily a sensory nerve. The lingual nerve can be stimulated to induce the patient's brain to stimulate the hypoglossal nerve to increase the opening of the airway. In other words, stimulating the lingual nerve can induce a reflex action that leads to activation of the hypoglossal nerve and the muscles innervated thereby rather than directly stimulating the hypoglossal nerve. As in the other variation described above, no sensing is conducted of the signals in the nerve being stimulated, which in this case is the lingual nerve.

In a third embodiment of the method, the controller can be programmed to provide stimulation at a predetermined interval without either detecting a physical process or requiring feedback from the nerve being stimulated. In this method, the stimulation interval can be determined from the patient's nighttime basal metabolism, e.g., based on the patient's observed nighttime resting respiratory rate. The resultant timing of the stimulation pulse trains will closely simulate the patient's normal nighttime respiration cycle. For example, a train of stimulus pulses can be applied for about 2 seconds to about 3 seconds, and more particularly, for about 2½ seconds, with a wait of at least 2 seconds to about 3 seconds between the pulse trains. The pulse trains can each have an amplitude that is at or greater than the patient's activation threshold, up to about 20% above the patient's activation threshold, for example. In this embodiment, the stimulation is provided at predetermined rate or pace without the added complexity of closed-loop feedback.

Other potential applications of this method, besides treating obstructive sleep apnea (OSA), include supplemental nerve stimulation to keep the airway open and treat snoring or for treating hypopnea, or countering motor activation of the tongue during a seizure to prevent the tongue from protruding and being injured during the seizure, for example. Other health problems related to the patency of a patient's airway also can be treated using methods provided by the present invention.

Although the invention has been shown and described with respect to certain illustrated embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiments of the invention. In addition, while a particular feature of the invention may have been described above with respect to only one of several illustrated embodiments, such a feature may be combined with one or more other features of the other embodiment, as maybe desired and advantageous for any given or particular application.

What is claimed is:

1. A method for treating sleep apnea, comprising:
   continuously electrically stimulating at least one fascicle of a genioglossus nerve at a predetermined amplitude of about 10% less than the threshold amplitude necessary to activate a first muscle of a patient up to 1% less than the threshold amplitude necessary to activate the first muscle of the patient; and
   continuously electrically stimulating at least one fascicle of a styloglossus nerve at a predetermined amplitude of about 10% less than the threshold amplitude necessary to activate a second muscle of a patient up to 1% less than the threshold amplitude necessary to activate the second muscle of the patient,
   where the first muscle and the second muscle are functionally opposite muscles.

* * * * *

UNITED STATES PATENT AND TRADEMARK OFFICE
CERTIFICATE OF CORRECTION

| | | |
|---|---|---|
| PATENT NO. | : 7,680,538 B2 | Page 1 of 1 |
| APPLICATION NO. | : 11/109338 | |
| DATED | : March 16, 2010 | |
| INVENTOR(S) | : Durand et al. | |

It is certified that error appears in the above-identified patent and that said Letters Patent is hereby corrected as shown below:

In column 6, line 24, delete "maybe" and insert --may be--.

Signed and Sealed this

Fourth Day of May, 2010

David J. Kappos
*Director of the United States Patent and Trademark Office*